United States Patent
Lee et al.

(10) Patent No.: US 10,508,997 B1
(45) Date of Patent: Dec. 17, 2019

(54) METHOD OF ANALYZING FINES MIGRATION IN MULTIPHASE FLOW IN SEDIMENT LAYER USING X-RAY COMPUTED TOMOGRAPHY IMAGE

(71) Applicant: Korea Institute Of Geoscience And Mineral Resources, Daejeon (KR)

(72) Inventors: Joo-Yong Lee, Daejeon (KR); Min-Hui Lee, Gongju-si (KR); Gyeol Han, Daejeon (KR); Tae-Hyuk Kwon, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 0 days.

(21) Appl. No.: 16/390,249

(22) Filed: Apr. 22, 2019

(30) Foreign Application Priority Data

May 28, 2018 (KR) .......................... 10-2018-0060668

(51) Int. Cl.
| | |
|---|---|
| *G01N 23/00* | (2006.01) |
| *G01N 23/046* | (2018.01) |
| *G01N 33/24* | (2006.01) |
| *G06T 5/00* | (2006.01) |
| *G06T 7/246* | (2017.01) |
| *G06T 7/62* | (2017.01) |

(52) U.S. Cl.
CPC .......... *G01N 23/046* (2013.01); *G01N 33/24* (2013.01); *G06T 5/002* (2013.01); *G06T 7/246* (2017.01); *G06T 7/62* (2017.01); *G01N 2223/401* (2013.01); *G01N 2223/616* (2013.01); *G06T 2207/10081* (2013.01); *G06T 2207/20072* (2013.01); *G06T 2207/30181* (2013.01)

(58) Field of Classification Search
CPC ................. G01N 23/046; G01N 33/24; G01N 2223/401; G01N 2223/616; G06T 7/62; G06T 7/246; G06T 5/002; G06T 2207/10081; G06T 2207/20072; G06T 2207/30181

See application file for complete search history.

(56) References Cited

U.S. PATENT DOCUMENTS

| | | | |
|---|---|---|---|
| 6,094,619 A * | 7/2000 | Noetinger | G01V 1/282 |
| | | | 702/12 |
| 9,170,215 B2 * | 10/2015 | O'Hare | G01N 23/046 |
| 9,448,189 B2 * | 9/2016 | Korkin | G01N 23/12 |

FOREIGN PATENT DOCUMENTS

| | | |
|---|---|---|
| KR | 2002-0067036 A | 8/2002 |
| KR | 2008-0039498 A | 5/2008 |
| KR | 100972624 B1 | 7/2010 |

(Continued)

OTHER PUBLICATIONS

Seol et al., "Experimental and numerical observation of hydrate reformation during depressurization in a core-scale reactor," 2011, Energy Fuels, vol. 25, No. 1099-1110. (Year: 2011).*

(Continued)

*Primary Examiner* — Kiho Kim
(74) *Attorney, Agent, or Firm* — Harness, Dickey & Pierce, P.L.C.

(57) ABSTRACT

A method of analyzing fines migration in a multiphase flow in a sediment layer using X-ray computed tomography (CT) image includes, preparing an X-ray CT image analysis sample; analyzing an X-ray CT image during a depressurization process; calibrating and calculating a fines content; and estimating a fines migration analysis result.

23 Claims, 15 Drawing Sheets

(56) References Cited

FOREIGN PATENT DOCUMENTS

KR          101110787 B1    2/2012
KR        2013-0094564 A    8/2013

OTHER PUBLICATIONS

Schmitz et al., "Tomographic imaging of transient multiphase flow in bubble columns," 2000, Chemical Engineering Journal, vol. 77, pp. 99-104. (Year: 2000).*

Turner et al., "Three-dimensional imaging of multiphase flow in porous media," 2004, Physica A, vol. 339, pp. 166-172. (Year: 2004).*

Wang et al., "Analysis of the influence of wettability on permeability in hydrate-bearing porous media using pore network models combined with computed tomography," Journal of Natural Gas Science and Engineering, vol. 26, pp. 1372-1379. (Year: 2015).*

Gyeol Han et al., "Depressurization-Induced fines Migration in Sediments Containing Methane Hydrate: X-Ray Computed Tomography Imaging Experiments", Journal of Geophysical Research: Solid Earth, (2018), 123, pp. 1-20.

Korean Notice of Preliminary Rejection for Korean Patent Application No. 10-2018-0060668 dated Jun. 27, 2018.

Korean Notice of Allowance for Korean Patent Application No. 10-2018-0060668 dated Aug. 2, 2018.

* cited by examiner

FIG. 1

| Parameter | Sand | | Fines | |
|---|---|---|---|---|
| Soil type | Ottawa 20-30 sand | F110 sand | Silica silt | Kaolinite |
| Mean grain diameter (μm) | 722 | 142 | 20 | 10 |
| Specific gravity | 2.65 | 2.65 | 2.65 | 2.59 |
| $e_{max}/e_{min}$ | 0.742/0.502$^a$ | 0.85/0.54$^a$ | 1.51/0.67$^a$ | -- |
| Plastic limit / Liquid limit | -- | -- | -- | 43/60 |
| Void ratio of fines at 1 kPa $e_{1kPa}$$^b$ | | | 0.7 | 1.6 |
| Specific surface area (m²/g) | 0.0031$^c$ | 0.016$^c$ | 0.67$^c$, 4.2$^d$ | 16$^c$, 41$^d$ |
| Particle shape image | | | | |

| Sample preparation | Drawings |
|---|---|
| From image after gas injection but before, hydrate formation. |  |
| $M_{total} = M_{sand} + M_{fines} + M_{water}$ | |
| Water content, $w = M_{water} / (M_{sand} + M_{fines})$ | |
| Initial fines content, $FC_{ini} = M_{fines} / (M_{sand} + M_{fines})$ | |
| $M_{sand} = (1 - FC_{ini}) \cdot M_{total} / (1 + w)$ |  |

FIG. 8

| Depressurization | Drawings |
|---|---|
| From image after depressurization. | |
| $M_{total\_f} = M_{solid} + M_{fines\_f} + M_{water\_f}$ | |
| $M_{total\_f} = M_{solid\_f} + \rho_w V_{gas}$ | |
| $M_{void\_f} = M_{total\_f} - M_{solid\_f}$ | |
| $M_{void\_f} = M_{fine\_f} + M_{water\_f}$ | |
| $V_{solid} = M_{solid} / G_s \rho_w$ | |
| $V_{void} = V_{total} - V_{solid}$ | |
| $M_{void} = \rho_w V_{void}$ | |

| Calibration & Calculation Result | Drawings |
|---|---|
| $\Delta M = M_{total\_f} - M_{void}$ |  |
| $M_{fines\_f} = \Delta M \cdot G_s / (G_s - 1)$ | |
| $FC_f = M_{fines\_f} / (M_{fines\_f} + M_{sand})$ | |
| $FC_f = (M_{total\_f} - V_{total} \cdot \rho_w) \cdot G_s / (G_s - 1) - M_{sand}$ | |
| $FC_{f,\,calibrated} = \alpha \cdot FC_f + \beta$ | |

METHOD OF ANALYZING FINES MIGRATION IN MULTIPHASE FLOW IN SEDIMENT LAYER USING X-RAY COMPUTED TOMOGRAPHY IMAGE

CROSS-REFERENCE TO RELATED APPLICATION

This application claims priority to Korean Patent Application No. 10-2018-0060668 filed on May 28, 2018, and all the benefits accruing therefrom under 35 U.S.C. § 119, the contents of which is incorporated by reference in its entirety.

BACKGROUND OF THE INVENTION

1. Field of the Invention

The present disclosure relates to a method of analyzing fines migration in a multiphase flow in a sediment layer using an X-ray computed tomography (CT) image. More specifically, the present disclosure relates to a method of analyzing fines migration in a multiphase flow of water and gas in a sediment layer, based on X-ray CT images, that appears during hydrate dissociation, using X-ray CT images taken step-wisely during an entire experiment for monitoring a process of a production experiment of gas hydrate (GH) in real time.

2. Description of the Related Art

An X-ray CT is a typical method of non-destructive monitoring, which visualizes the cross-section of an object through which an X-ray has been transmitted. X-ray CT equipment consists mainly of an X-ray generator, an X-ray detector and a table on which an object is placed. The X-ray generated by the X-ray generator passes through the object and reaches the X-ray detector. The inside of the object is visualized by inversely estimating the X-ray reached at this time. Generally, an X-ray CT can be classified as an industrial X-ray CT or a medical X-ray CT. An industrial X-ray CT can use a high-power X-ray generator and generally, the object to be detected rotates. A medical X-ray CT uses an appropriate level of energy on the human body while an X-ray generator and a detector rotates.

X-ray CT scans objects at regular intervals and shoots one image at a time, and one image is called a slice. A slice consists of several pixels, and a pixel is the smallest unit of expression that an X-ray can be represented with. The pixels of an X-ray contain information of the intensity of the X-ray. It is shown through a ratio of an energy level in the X-ray generator to an energy level in the detector, and at this time, an amount decrease is explained by Beer's law. A significant factor of intensity reduction is proportional to the energy in the X-ray generator, the distance of where the X-ray passed by, and a linear reduction coefficient, which is an intrinsic value of a material. Since the energy of the X-ray in the X-ray generator corresponds with the distance of where the X-ray passed by, only the linear reduction coefficient of the material affects the intensity reduction. This constant is a material-specific constant, proportional to the density of the material and the weight of the atom. The higher the density of the material, the greater the reduction, and even at the same density, the higher the weight of the atom, the greater the reduction. The value of the intensity detected by the detector is called the CT value.

Changes in CT values in the pixels of each slice are obtained as information when performing non-destructive monitoring using X-ray CT equipment. Because it is not possible to deduce what changes have occurred with only the changes in CT values, an experiment has to be conducted to find a value that can calibrate these CT values. Through a sand production experiment, what changes is the phase of the material, and what changes the most is the density. A change in density causes a difference in intensity. In consideration of this, various materials, of which their densities are known, are put into a cell used previously in the experiment, and the CT value at this time is measured, and density calibration is performed by plotting the relationship between the CT value and the density.

Patent Document 1 discloses a method of measuring a void ratio of fine soil via an X-ray CT, wherein the void ratio of soil is measured by subjecting the soil sample to X-ray CT. At this time, since there are soil particles that are smaller than the minimum voxel size of the X-ray CT image, it is possible to measure the void ratio of soil through X-ray CT even for fine soil having voids that are difficult to visualize. Patent 1 discloses a method of measuring a void ratio of soil, which includes acquiring an X-ray CT image of a standard sample of soil, having a soil particle size smaller than a minimum voxel size of the X-ray CT image, of which its void ratio is already known, obtaining a CT value for each voxel in the X-ray CT image, calculating a CT representative value of the X-ray CT from each CT value, acquiring data of the CT representative value and the void ratio of the soil, constructing a database of a plurality of void ratios and CT representative values of a plurality of types of standard soil samples having different void ratios, calculating CT values and CT representative values for each voxel from the X-ray CT image of the soil sample to be measured, and obtaining a void ratio corresponding to the calculated CT representative value from the pre-constructed database of void ratios and CT representative values, to measure the void ratio of the soil to be measured.

Each voxel in a conventional X-ray CT image represents intensity that indicates the degree of attenuation of the X-ray due to density. Therefore, an analysis of contents using classification of materials using various segmentation techniques and analysis results should be preceded. In the case of single-phase flow, it is possible to analyze the fines content using only the existing segmentation technique. However, in the case of multiphase flow, in which gas, generated during a production process of gas hydrate, moves together with water, it has been difficult to quantitatively analyze the movement of the fine particles using the segmentation method alone.

As a prior art, there is Granted Korean Patent Publication No. 10-1110787.

SUMMARY OF THE INVENTION

The present disclosure is directed to providing a method of analyzing fines migration in a sediment layer due to a multiphase flow during a production of gas hydrate, by a voxel-scale analysis of an X-ray CT image.

According to an aspect of the present disclosure, a method of analyzing fines migration in a multiphase flow in a sediment layer using X-ray CT image, may include, preparing an X-ray CT image analysis sample; analyzing an X-ray CT image during a depressurization process; calibrating and calculating fines content; and estimating a fines migration analysis result.

Further, the preparing the X-ray CT image analysis sample may include, obtaining an X-ray CT image after gas injection prior to gas hydrate production and performing a voxel-scale based analysis.

Further, the preparing the X-ray CT image analysis sample may be premised on, a first assumption that water and the fine particles are homogeneously distributed throughout the sample, and a second assumption that mass of sand per voxel ($M_{sand}$) is constant during the depressurization process.

Further, the analyzing the X-ray CT image during the depressurization process may include, classifying positions of gas bubbles based on threshold values obtained through a histogram analysis to calculate only the volume of the gas bubbles, and calculating the volume of fine particles that take up space in a constant volume as a volume of water divided by a number of voxels having gas therein of the entire sample, which is considered as a volume of each voxel, to calculate mass of the fine particles in each of the gas voxels.

Further, the calibrating and calculating the fines content may include, comparing the calculated fines content with a result of sampling after an experiment, to calculate a calibration coefficient, and finally calculating the fines content by applying the calibration coefficient.

Further the estimating the fines migration analysis result may include, estimating a change in the fines content at each position of the sample in each step of the depressurization process by using calculation results of the calculated fines content.

Further, the preparing the X-ray CT image analysis sample may further include, calculating Equation b-11 to Equation b-14.

Further, the analyzing the X-ray CT image during the depressurization process may include, calculating Equation b-21 to Equation b-26.

Further, the calibrating and the calculating the fines content may include, calculating Equation c-1 to Equation c-5.

According to another aspect of the present disclosure, an apparatus for carrying out a method of analyzing fines migration in a multiphase flow in a sediment layer using an X-ray CT image, may include, a high pressure cell provided with, a body part in which a center sample is located, a fluid injection port on one side of the body part, and a fluid discharge port on an opposite side of the body part; and a temperature sensor and a pressure sensor provided in the fluid injection port and the fluid discharge port.

Further, the apparatus may further include, a methane cylinder for supplying methane, connected to the fluid injection port; a syringe pump connected to the methane cylinder; a rear pressure gauge connected to the fluid discharge port; a scale for measuring only mass of water from gas and water discharged through an outlet of the rear pressure gauge; and a gas collector for collecting dry gas discharged through the outlet of the rear pressure gauge.

Further, the high pressure cell may further include, a screen disposed between the outlet of the fluid discharge port and the center sample; and a transparent window through which an inner part of the outlet of the fluid discharge port is reflected.

Further, the apparatus may further include, a glass bead drawn into the body part.

According to yet another aspect of the present disclosure, a system for carrying out a method of analyzing fines migration in a multiphase flow in a sediment layer using an X-ray CT image, may include, an X-ray CT imaging part for taking a fines migration image in a sediment layer; and a server for executing a fines migration analysis method using a photographed image of the X-ray CT imaging part, wherein the server comprises, an input part for applying a photographed image taken by the X-ray CT imaging part; an editing part for removing noise of the photographed image in the input part, according to an algorithm of at least one preset gas hydrate formation amount predicting method program; an analyzer for analyzing the fines migration in the photographed image from which the noise is removed; a calculating part for calculating the fines migration from analysis data of the analyzer; a calibrating part for calibrating the fines migration from calculation data of the calculating part; a result part for calculating a fines migration result from calibration data of the calibrating part; a determination part for determining a fines migration analysis result based on the results from the result part and for saving the photographed image in a storage area which is classified according to state depending on the determined result; and a communication part for transmitting a message informing the determined result to a pre-registered terminal.

According to yet another aspect of the present disclosure, a storage medium storing a computer program for implementing any of the above-mentioned methods.

The details of other embodiments are included in the 'detailed description of the invention' and the accompanying drawings.

The advantages and/or features of the present invention and the manner of achieving them will become apparent by reference to various embodiments described in detail below with reference to the accompanying drawings.

However, the present invention is not limited to the configurations of the embodiments described below, but may be embodied in various other forms, and each embodiment disclosed in this specification is intended to be illustrative only, and it will be understood by those of ordinary skill in the art that various changes in form and details may be made therein without departing from the spirit and scope of the invention as defined by the appended claims.

According to the present disclosure, it is possible to improve the accuracy of a monitoring technique using X-ray CT images by developing and applying a technique for analyzing the movement of fine particles flowing into the stratum cores during a multiphase flow.

BRIEF DESCRIPTION OF THE DRAWINGS

FIG. 1 is a graph showing physical properties of sediments used in a method of analyzing fines migration in a multiphase flow in a sediment layer using x-ray CT image of an embodiment of the present disclosure.

FIG. 8 is a graph showing a voxel-scale analysis procedure for estimating the weight of the fine particles in the depressurization process of FIG. 4.

DETAILED DESCRIPTION OF THE INVENTION

Figure 2:
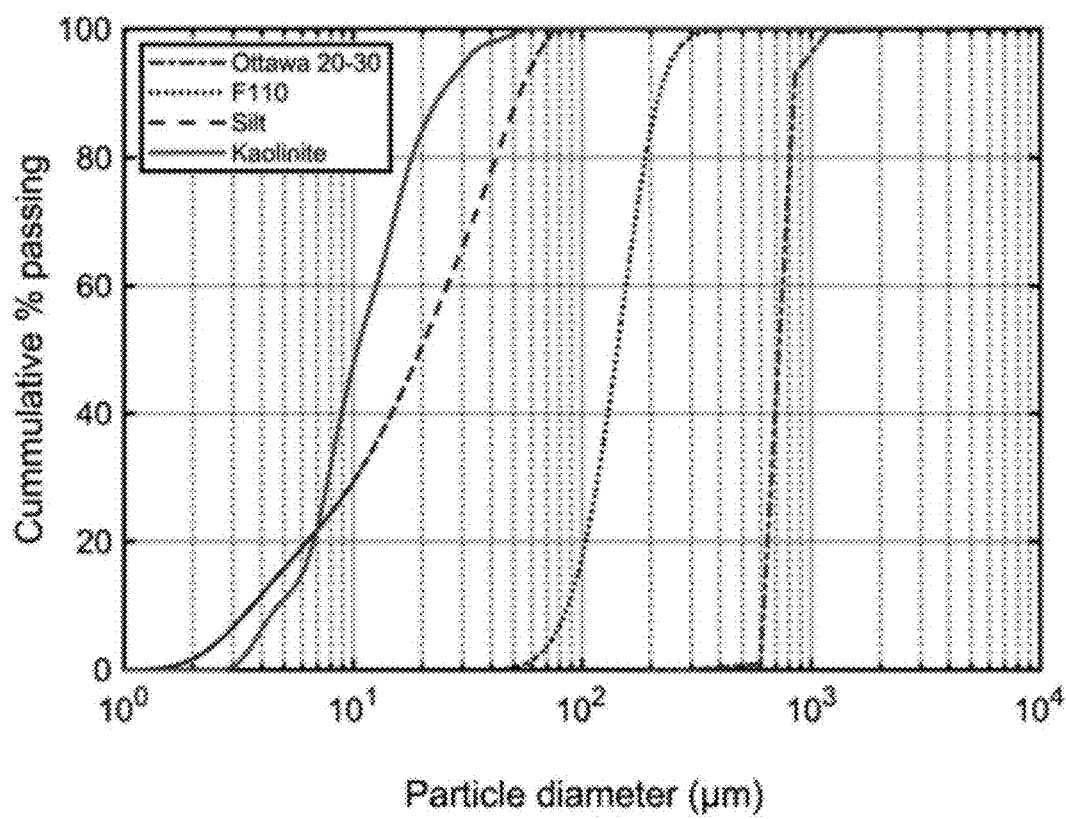
FIG. 2 is a graph showing particle size distribution of the sediment used in FIG. 1.

Hereinafter, an exemplary embodiment of the present invention will be described in detail with reference to accompanying drawings.

Before describing the present invention in detail, terms and words used herein should not be construed in an ordinary or dictionary sense and should not be construed as limiting the invention to the inventors of the present invention in the best way possible, and it is to be understood that the concepts of various terms can be properly defined and used, and further, these terms and words should be construed as meaning and concept consistent with the technical idea of the present invention.

That is, the terms used herein are used only to describe preferred embodiments of the present invention, and are not intended to specifically limit the contents of the present invention, and it should be noted that this is a defined term considering that many possibilities of the present invention.

Also, in this specification, the singular forms "a", "an", and "the" include plural referents unless the context clearly dictates otherwise, and similarly it should be understood that even if they are expressed in plural they may include singular meaning.

Where a component is referred to as "comprising" another component throughout this specification, unless specified otherwise, this means the component does not exclude any other element but may further include any other element.

Further, when it is stated that an element is "inside or connected to another element", this element may be directly connected to another element or may be installed in contact with it, or may be installed spaced apart with a predetermined distance, and in the case where a component is installed to be spaced apart With a predetermined distance, a third component or means for fixing or connecting the component to another component may be present, and it should be noted that the description of the third component or means may be omitted.

On the other hand, it should be understood that there is no third component or means when an element is described as being "directly coupled" or "directly connected" to another element.

Likewise, other expressions that describe the relationship between the components, such as "between" and "right between ~", or "neighboring to" and "directly adjacent to" and such should be understood in the same spirit.

Further, in this specification, when terms such as "one surface", "other surface", "one side", "other side", "first", "second" and such are used, it is to clearly distinguish one component from another, and it should be understood that the meaning of the component is not limited by such term.

It is also to be understood that terms related to positions such as "top", "bottom", "left", "right" in this specification are used to indicate relative positions in the drawings for the respective components, and unless an absolute position is specified for these positions, it is not to be understood that these position-related terms refer to absolute positions.

Furthermore, in the specification of the present invention, the terms "part", "unit", "module", "device" and the like mean a unit capable of handling one or more functions or operations, and may be implemented as a hardware or software, or a combination of hardware and software.

In addition, in this specification, the same reference numerals are used for the respective constituent elements of the drawings, and the same constituent elements are denoted by the same reference numerals even if they are shown in different drawings, that is, the same reference numerals indicate the same components throughout this specification.

It is to be understood that the size, position, coupling relationships and such, of each component constituting the present invention in the accompanying drawings, may be partially exaggerated or reduced or omitted to be able to sufficiently clearly convey the scope of the invention or for convenience of describing, and therefore the proportion or scale thereof may not be rigorous.

Also, in the following description of the present invention, a detailed description of a configuration that is considered to unnecessarily obscure the gist of the present invention, for example, a known technology including the prior art, may be omitted.

FIG. 1 is a graph showing physical properties of sediments used in a method of analyzing fines migration in a multiphase flow in a sediment layer using x-ray CT image of an embodiment of the present disclosure.

FIG. 2 is a graph showing particle size distribution of the sediment used in FIG. 1.

Figure 3A:
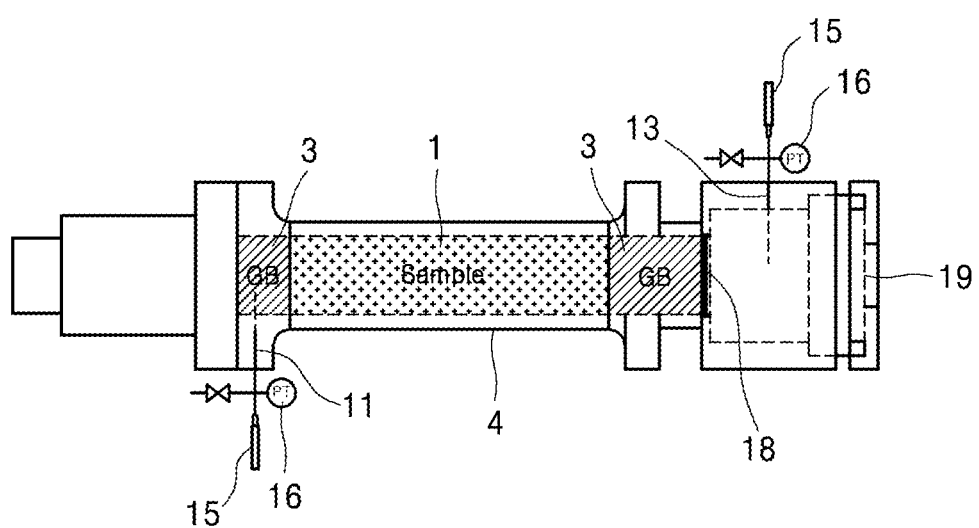
FIG. 3A is a schematic view of a high-pressure cell and a cell filled with a sample of FIG. 1.
Figure 3B:
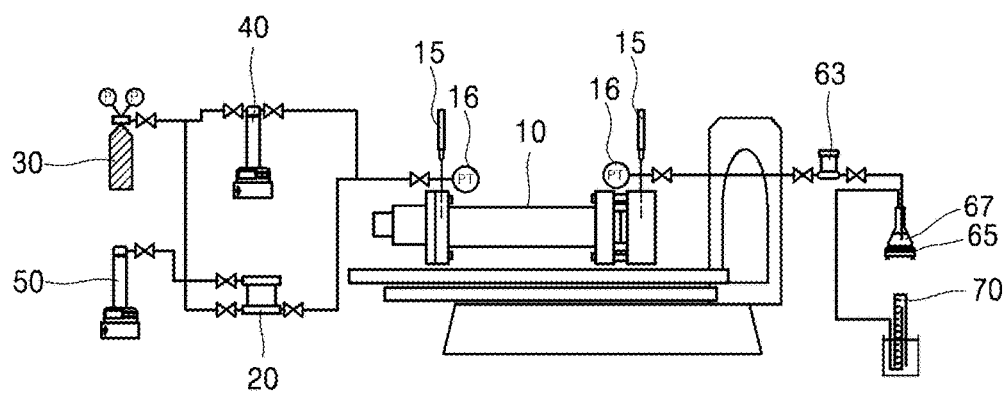
FIG. 3B is a schematic view showing the whole experimental system for producing gas hydrate of FIG. 1.
Figure 3C:
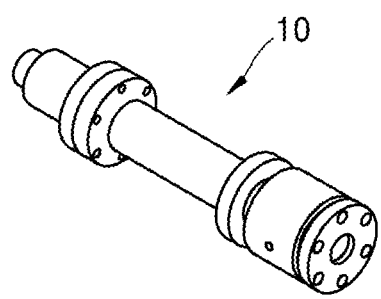
FIG. 3C is a perspective view of FIG. 3A.

FIG. 3A is a schematic view of a high-pressure cell and a cell filled with a sample of FIG. 1, FIG. 3B is a schematic view showing the whole experimental system for producing gas hydrate of FIG. 1, and FIG. 3C is a perspective view of FIG. 3A.

Figure 4:
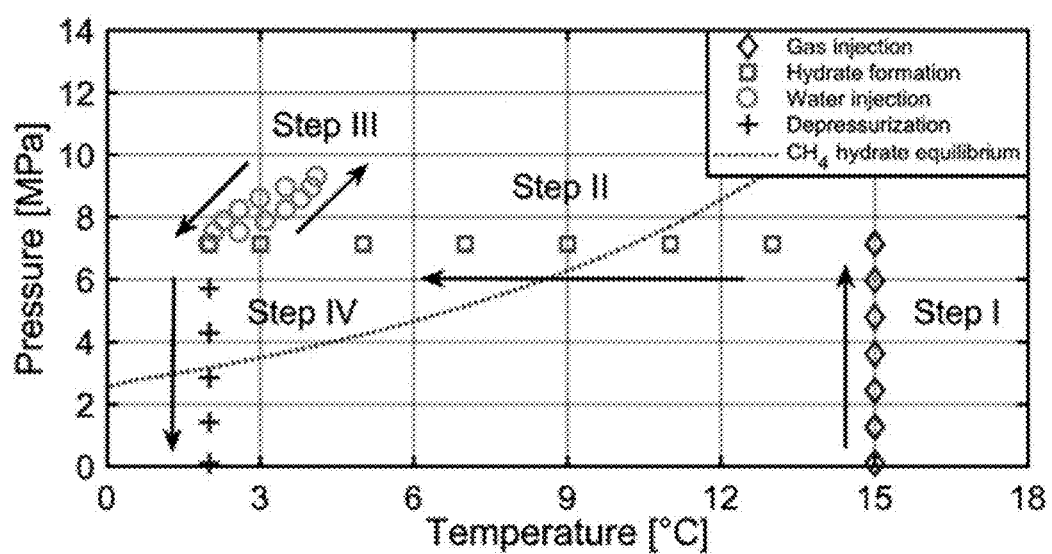
FIG. 4 is a pressure-temperature tracing graph during gas injection, hydrate formation, water injection and depressurization process of the experimental procedure of a method of analyzing fines migration in a multiphase flow in a sediment layer using an X-ray CT image of an embodiment of the present disclosure.

FIG. 4 is a pressure-temperature tracing graph during gas injection, hydrate formation, water injection and depressurization process of the experimental procedure of a method of analyzing fines migration in a multiphase flow in a sediment layer using an X-ray CT image of an embodiment of the present disclosure.

Figure 5:
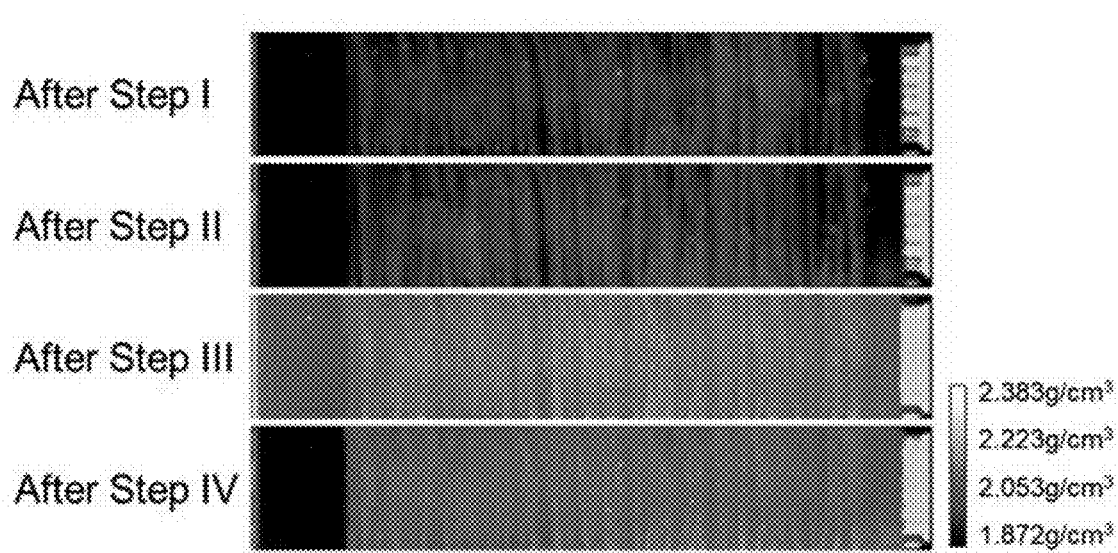
FIG. 5 is a representative photograph of an X-ray CT image taken during gas injection, gas hydrate formation, water injection, and depressurization.

FIG. 5 is a representative photograph of an X-ray CT image taken during gas injection, gas hydrate formation, water injection, and depressurization.

Figure 6:
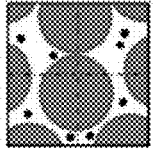
FIG. 6 is a graph showing a voxel-scale analysis procedure for estimating the sand mass in the sample preparation process of FIG. 4.
Figure 6:
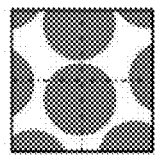

FIG. 6 is a graph showing a voxel-scale analysis procedure for estimating the sand mass in the sample preparation process of FIG. 4.

Figure 7:
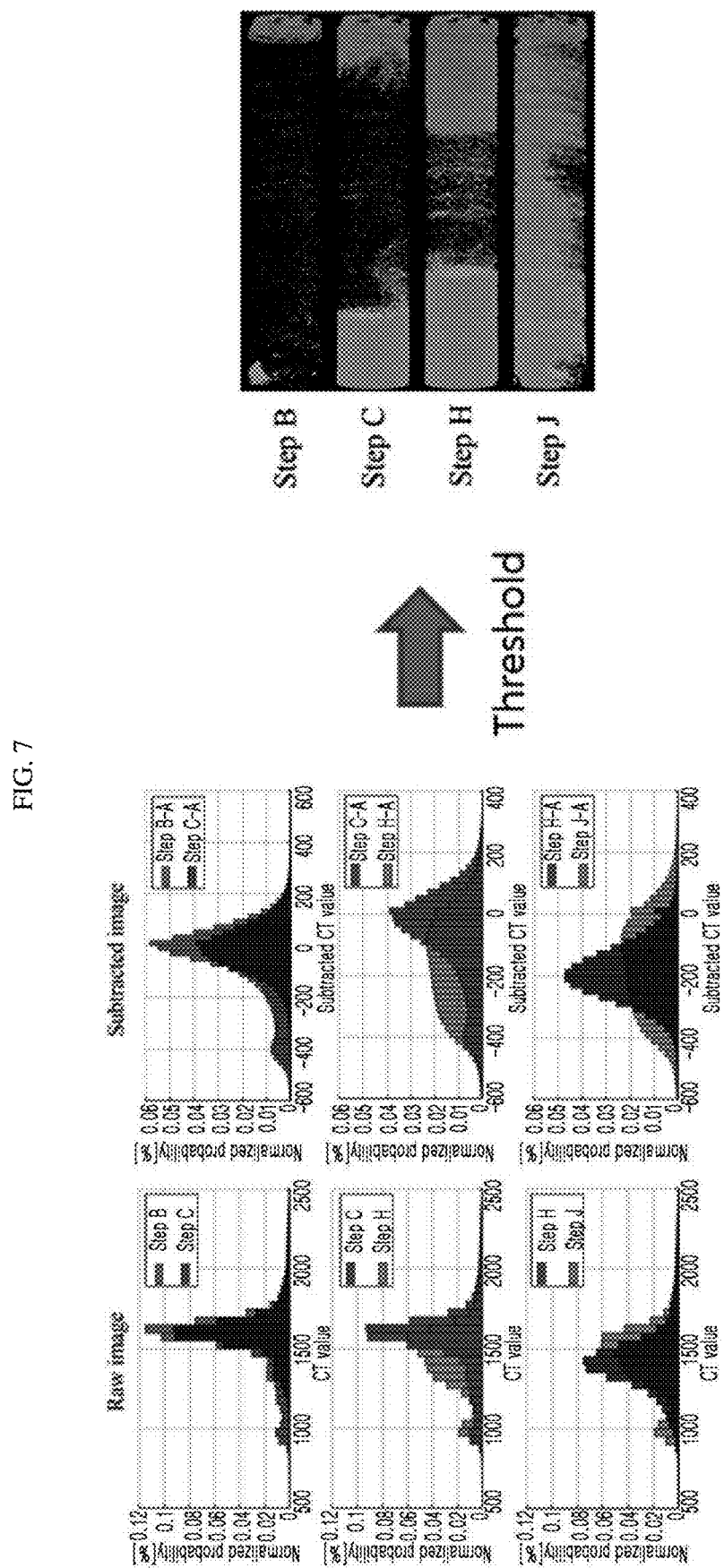
FIG. 7 is a photograph showing the histogram change of the X-ray CT value of the sample during depressurization of FIG. 4 and the spatial change of gas bubbles generated during the depressurization.

FIG. 7 is a photograph showing the histogram change of the X-ray CT value of the sample during depressurization of FIG. 4 and the spatial change of gas bubbles generated during the depressurization.

FIG. 8 is a graph showing a voxel-scale analysis procedure for estimating the weight of the fine particles in the depressurization process of FIG. 4.

Figure 9:
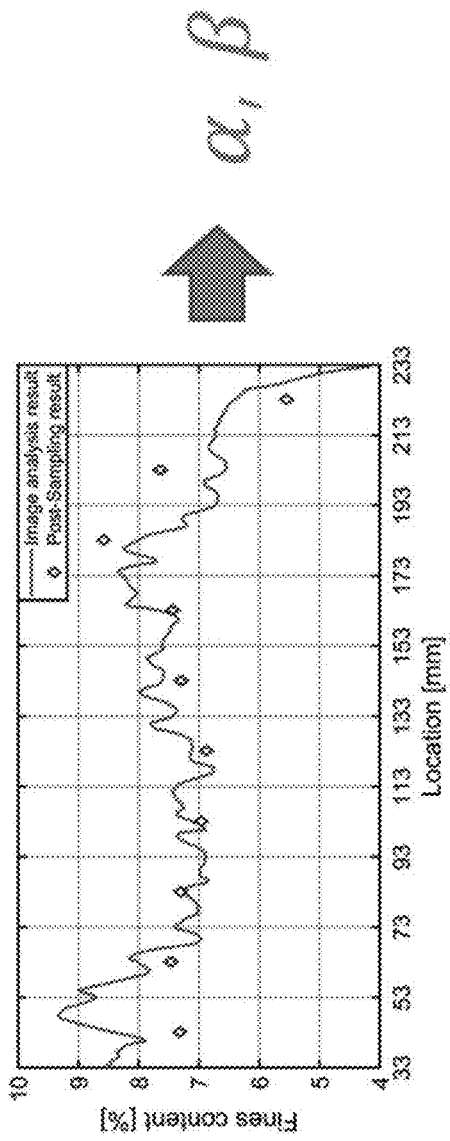
FIG. 9 is a graph for calculating a calibration coefficient by comparing the calculated fines content with the sampling result after the experiment.

FIG. 9 is a graph for calculating a calibration coefficient by comparing the calculated fines content with the sampling result after the experiment.

Figure 10:
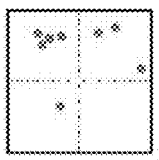
FIG. 10 is a chart showing a voxel-scale analysis procedure for calibrating the fines content by applying a mass of the fine particles and a calculated calibration coefficient.

FIG. 10 is a chart showing a voxel-scale analysis procedure for calibrating the fines content by applying a mass of the fine particles and a calculated calibration coefficient.

Figure 11:
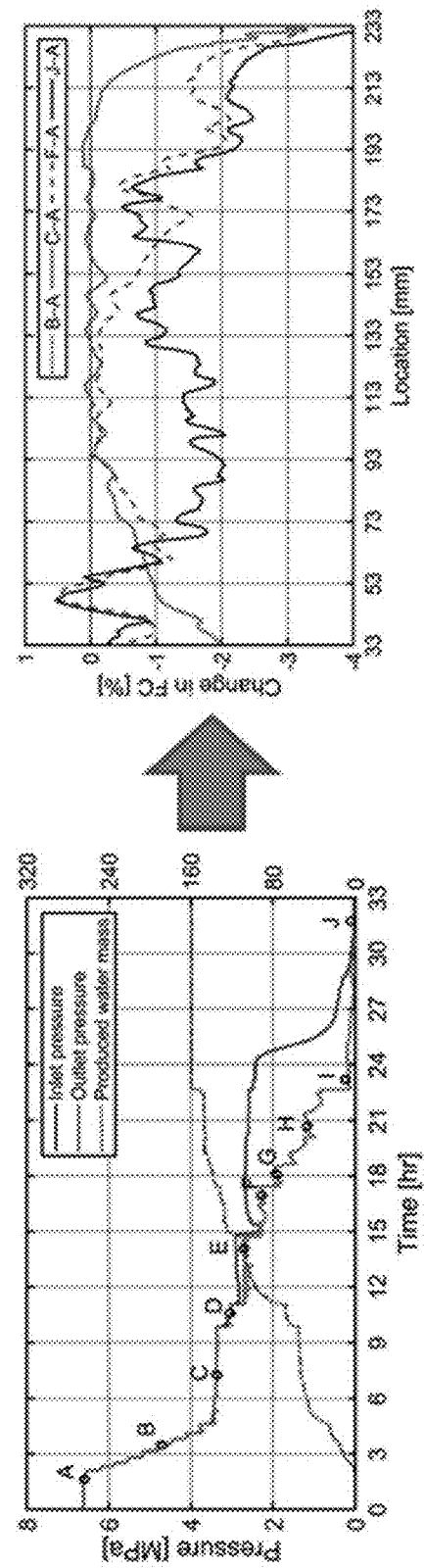
FIG. 11 is a graph showing changes in fines content of each step.

FIG. 11 is a graph showing changes in fines content of each step.

Figure 12:
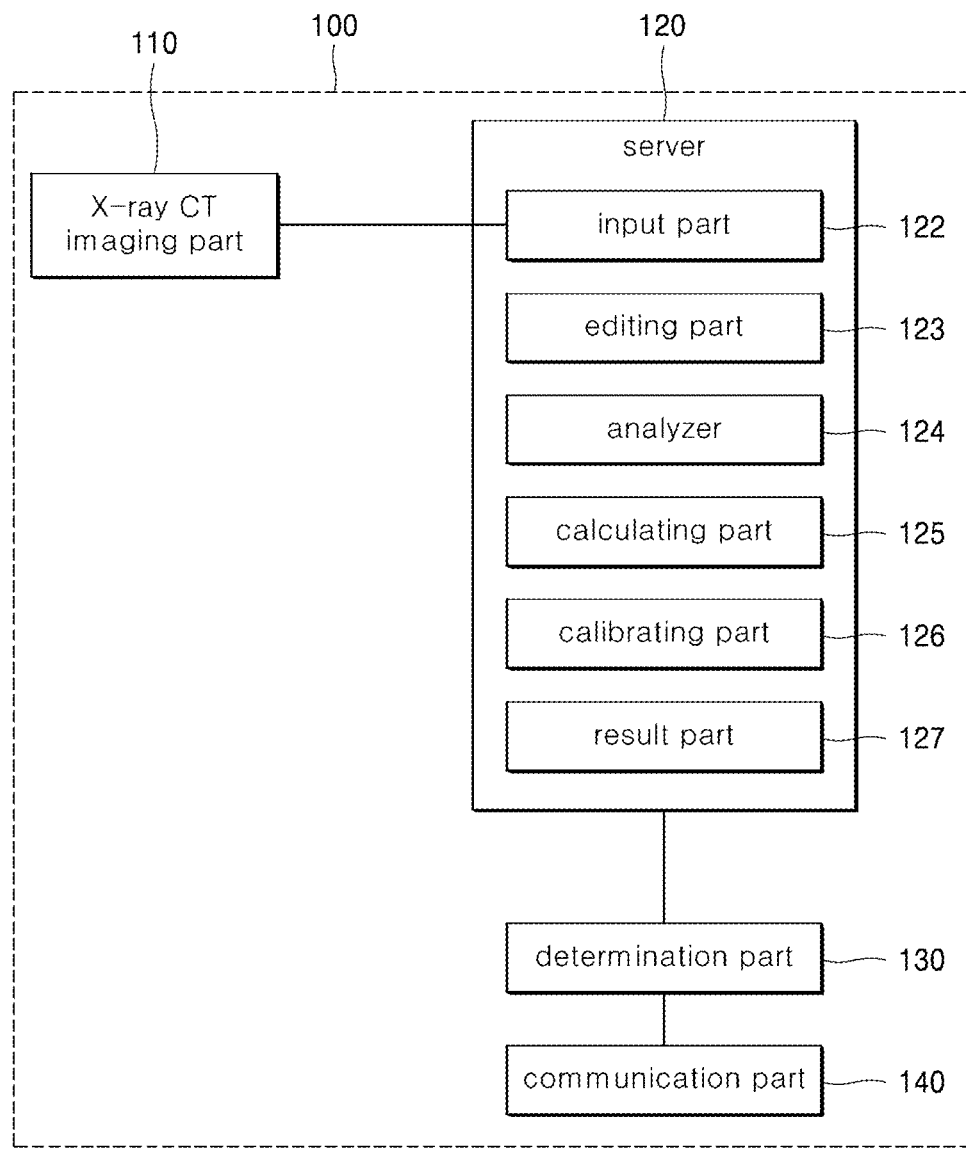
FIG. 12 is a configuration diagram of a system of an apparatus for acquiring an X-ray CT image at each step of an experiment of an embodiment of the present disclosure.

FIG. 12 is a configuration diagram of a system of an apparatus for acquiring an X-ray CT image at each step of an experiment of an embodiment of the present disclosure.

Figure 13:
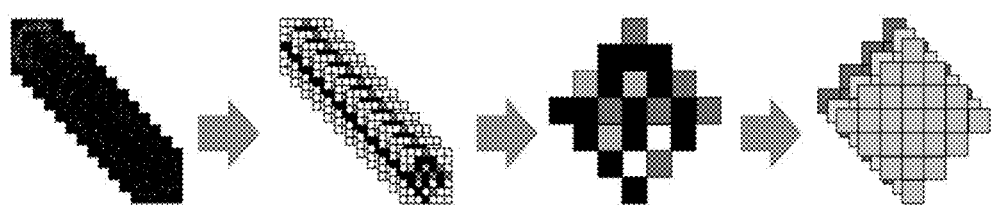
FIG. 13 is a schematic view showing a method of predicting a production amount of a gas hydrate.

FIG. 13 is a schematic view showing a method of predicting a production amount of a gas hydrate.

A method of analyzing fines migration in a multiphase flow in a sediment layer using X-ray CT image, includes, preparing an X-ray CT image analysis sample; analyzing an X-ray CT image during a depressurization process; calibrating and calculating fines content; and estimating a fines migration analysis result.

In the step of preparing the X-ray CT image analysis sample, an X-ray CT image is obtained after gas injection prior to gas hydrate production, and a voxel-scale based analysis is performed.

The step of preparing the X-ray CT image analysis sample is premised on a first assumption that water and the fine particles are homogeneously distributed throughout the sample, and a second assumption that mass of sand per voxel ($M_{sand}$) is constant during the depressurization process.

The preparing the X-ray CT image analysis sample further includes calculating Equation b-11 to Equation b-14.

$$M_{total0} = M_{sand} + M_{fines0} + M_{water} \quad \text{[Equation b-11]}$$

wherein, $M_{total0}$: total mass per voxel, $M_{sand}$: mass of sand per voxel, $M_{fines0}$: mass of fine particles per voxel, $M_{water}$: mass of water per voxel.

$$w = M_{water}/(M_{sand} + M_{fines0}) \quad \text{[Equation b-12]}$$

wherein, w: water content, $M_{water}$: mass of water per voxel, $M_{sand}$: mass of sand per voxel, $M_{fines0}$: mass of fine particles per voxel.

$$FC_{ini} = M_{fines0}/(M_{sand} + M_{fines0}) \quad \text{[Equation b-13]}$$

wherein $FC_{ini}$: initial fines content, $M_{fines0}$: mass of fine particles per voxel, $M_{sand}$: mass of sand per voxel.

$$M_{sand} = (1 - FC_{ini}) \cdot M_{total0}/(1+w) \quad \text{[Equation b-14]}$$

wherein, $M_{sand}$: mass of sand per voxel, $FC_{ini}$: initial fines content, $M_{total0}$: total mass per voxel, w: water content.

The step of analyzing the X-ray CT image during the depressurization process includes, classifying positions of gas bubbles based on threshold values obtained through a histogram analysis to calculate only the volume of the gas bubbles, and calculating the volume of fine particles that can take up space in a constant volume as a volume of water divided by a number of voxels having gas therein of the entire sample, considered as a volume of each voxel, to calculate mass of the fine particles in each of the gas voxels.

The step of analyzing the X-ray CT image during the depressurization process further includes calculating Equation b-21 to Equation b-26.

$$M_{total\_J} = M_{sand} + M_{fines\_J} + M_{water\_J} \quad \text{[Equation b-21]}$$

wherein, $M_{total\_J}$: total mass per voxel after depressurization, $M_{sand}$: mass of sand per voxel, $M_{fines\_J}$: mass of fine particles per voxel after depressurization, $M_{water\_J}$: mass of water per voxel after depressurization, $$M'_{total\_J} = M_{total\_J} + \rho_w \cdot V_{gas} \quad \text{[Equation b-22]}$$

wherein, $M_{total\_J}$: total mass per voxel after depressurization, $M'_{total\_J}$: total mass per voxel after water replaces gas by volume after depressurization, $\rho_w$: bulk density of voxel, $V_{gas}$: volume of gas per voxel.

$$M'_{total\_J} - M_{sand} = M_{void\_J} \quad \text{[Equation b-23]}$$

wherein, $M'_{total\_J}$: total mass per voxel after water replaces gas by volume after depressurization, $M_{sand}$: mass of sand per voxel, $M_{void\_J}$: void mass per voxel after depressurization.

$$M_{void\_J} = M_{fines\_J} + M_{water\_J} \quad \text{[Equation b-24]}$$

wherein, $M_{void\_J}$: void mass per voxel after depressurization, $M_{fines\_J}$: mass of fine particles per voxel after depressurization.

$$V_{sand} = M_{sand}/G_s \cdot \rho_w \quad \text{[Equation b-25]}$$

wherein, $V_{sand}$: volume of sand per voxel, $M_{sand}$: mass of sand per voxel, $G_s$: specific density of sediment particle, $\rho_w$: bulk density of voxel.

$$V_{void} = V_{total} - V_{sand} \quad \text{[Equation b-26]}$$

wherein, $V_{void}$: void volume per voxel, $V_{total}$: total volume per voxel, $V_{sand}$: volume of sand per voxel.

The step of calibrating and calculating the fines content includes, comparing the calculated fines content with a result of sampling after an experiment, to calculate a calibration coefficient, and finally calculating the fines content by applying the calibration coefficient.

The step of calibrating and the calculating the fines content further includes calculating Equation c-1 to Equation c-5.

$$\Delta M = M_{void\_J} - M_{void} \quad \text{[Equation c-1]}$$

wherein, $M_{void}$: void mass per voxel, $M_{void\_J}$: void mass per voxel after depressurization, $\Delta M$: difference of void mass per voxel before and after depressurization.

$$M_{fines\_J} = \Delta M \cdot G_s/(G_s - 1) \quad \text{[Equation c-2]}$$

wherein, $M_{fines\_J}$: mass of fine particles per voxel after depressurization, $\Delta M$: difference of void mass per voxel before and after depressurization, $G_s$: specific density of sediment particle.

$$FC_J = M_{fines\_J}/(M_{fines\_J} + M_{sand}) \quad \text{[Equation c-3]}$$

wherein, $FC_J$: fines content after depressurization, $M_{fines\_J}$: mass of fine particles per voxel after depressurization, $M_{sand}$: mass of sand per voxel.

$$FC_J = (M'_{total\_J} - V_{total} \rho_w) \cdot G_s/(G_s - 1) - M_{sand} \quad \text{[Equation c-4]}$$

wherein, $FC_J$: fines content after depressurization, $M'_{total\_J}$: total mass per voxel after depressurization, $V_{total}$: total volume per voxel, $\rho_w$: density of water, $G_s$: specific density of sediment particle, $M_{sand}$: mass of sand per voxel.

$$FC_{J\_calibrated} = \alpha \cdot FC_J + \beta \quad \text{[Equation c-5]}$$

wherein, $FC_{J\_calibrated}$: calibrated fines content, $\alpha$: calibration parameter, $FC_J$: fines content after depressurization, $\beta$: offset parameter.

In the step of estimating the fines migration analysis result, a change in the fines content at each position of the sample in each step of the depressurization process is estimated by using calculation results of the calculated fines content.

In a method of analyzing fines migration in a multiphase flow in a sediment layer using an X-ray CT image of the present disclosure, through a voxel-scale analysis based on mutually different densities of water and gas, the fines migration that appears in a multiphase flow, like that of a production process of gas hydrate, is analyzed. The density change of sediment that appears during the production process of gas hydrate and the change of X-ray CT images due to the same is caused mainly by the dissociation of gas hydrate, movement of sand particles, generation of gas bubbles, and fines migration. Therefore, by analyzing some premises and the change of the intensity of each voxel, in the end, it is possible to analyze fines migration in a multiphase flow. The method of analysis involves the process of gas bubble tracing, fines content analysis, sampling method, and application of a calibration coefficient obtained by comparison and so on, through data processing of X-ray CT images obtained throughout the whole analysis. In addition, the reliability of the method of analysis was verified by varying the particle size and the content distribution of the sand and fine particles, and finally, a method of quantitatively analyzing the fines migration in a multiphase flow using an X-ray CT image was provided.

In the present disclosure, a method of analyzing fines migration in a multiphase flow in a sediment layer using an X-ray CT image was provided. In order to analyze the movement of the fine particles, a fines content analysis must be performed prior thereto. For this, the X-ray CT images of the step of preparing a sample and the step of depressurization must be mutually compared. Among the factors causing the change of the X-ray CT images due to the density change in each process, there is no significant difference in particle movement due to the slow depressurization rate, and since the change of the difference of density of water and gas hydrated due to gas hydration dissociation is not great, it is possible to analyze fines migration if the generated gas bubbles are traced and the fines content is analyzed. In order to trace the gas bubbles, the change of CT values was determined using histogram analysis, and spatial information was obtained from threshold analysis. The fines content was determined by analyzing the position of the gas bubbles, the mass of the constituent, the volume, difference of content change and finally applying a calibration coefficient obtained from the sampling method.

The method of analyzing fines migration in a multiphase flow in a sediment layer using an X-ray CT image of the present disclosure will be described with reference to the drawings.

Referring to FIG. 1 and FIG. 2, in order to confirm the method of analyzing the fines migration provided in the present disclosure in the case of various particle sizes, two types of sand and fine particles were used. The sand sample used for the analysis was sand sample F110, and the characteristics of each sample are shown in FIG. 1, and the particle size distributions of the respective sand and fine particles are shown in FIG. 2.

The method of analyzing fines migration in a multiphase flow in a sediment layer using an X-ray CT image of the present disclosure may be implemented by an apparatus for analyzing fines migration in a multiphase flow in a sediment layer using an X-ray CT image. The apparatus for carrying out the method of analyzing fines migration in a multiphase flow in a sediment layer using an X-ray CT image according to an embodiment of the present disclosure may be configured to have, a high pressure cell 10 provided with, a body part 4 in which a center sample 1 is located, a fluid injection port 11 on one side of the body part 4, and a fluid discharge port 13 on an opposite side of the body part 4; and a temperature sensor 15 and a pressure sensor 16 provided in the fluid injection port 11 and the fluid discharge port 13.

The apparatus may further include, a methane cylinder 30 for supplying methane, connected to the fluid injection port 11; a syringe pump 40 and 50 connected to the methane cylinder 30; a rear pressure gauge 63 connected to the fluid discharge port 13; a scale 65 for measuring only mass of water from gas and water discharged through an outlet of the rear pressure gauge 63; and a gas collector 70 for collecting dry gas discharged through the outlet of the rear pressure gauge 63.

The high pressure cell 10 further includes, a screen 18 disposed between the outlet 14 of the fluid discharge port 13 and the center sample; and a transparent window 19 through which an inner part of the outlet of the fluid discharge port 13 is reflected.

The apparatus may further include a glass bead 3 drawn into the body part 4.

Referring to FIGS. 3A and 3B, a schematic view of the high pressure cell 10 used in the gas hydrate dissociation experiment is shown in FIG. 3A.

Referring to FIG. 3A, the body part of the high pressure cell 10 where the center sample 3 is located, may be made of aluminum, and the other parts may be made of stainless steel. The sample was molded to have a length of 230 mm and placed at the center of the high pressure cell 10, and the rest of the high pressure cell 10 was filled with glass beads 3 having a size of 250-420 μm to prevent the sample from moving. The temperature and pressure of an inlet and outlet were measured through a temperature sensor 15 and a pressure sensor 16 inserted through a fluid inlet port 11 on a left part and an outlet port 13 on a right part of the sample. A screen 18 was disposed between the outlet and the sample with a spacing of 100 μm to prevent damage to the experimental system through the production of sand. In addition, a space for collecting the produced sand was made between the outlet and the screen 18, and a transparent window 19 was formed on one side of the collection space so as to observe the sand production.

Referring to FIG. 3B, the overall system according to one embodiment of the present disclosure is shown. A temperature sensor 15 and a pressure sensor 16 are connected to each of the fluid inlet port 11 and the fluid outlet port 13 for measuring temperature and pressure changes. The quantity of flow and flow rate injected through the fluid inlet port are controlled through syringe-type pumps 40 and 50 connected to a methane cylinder 30 which supplies methane. The fluid discharge port 13 may be connected to the rear pressure gauge 63 to maintain pressure in a saturated state and to gradually reduce the pressure. Water from the gas and water discharged through the outlet part of the rear pressure gauge 63 was collected and measured by a scale 65 and the remaining dry gas was collected by a gas collector 70 to measure the amount of gas produced.

Further, FIG. 3B shows the experimental setup and measurements for synthesizing hydrate-containing sediments and performing depressurization during imaging of a sample using an X-ray CT scanner. The temperature of a vessel is controlled by circulating a temperature control fluid in a thermostatic bath (RW-1025G, Jeio Tech, Daejeon, Korea) through a silicone tube that is wrapped around the vessel. A temperature sensor 15 is connected to each of a thermocouple (K-type, KMTSS-010-018, Omega Engineering, Stamford, Conn., USA) and a resistance temperature detector (RTD, PT100, Korea Electric Heater, Korea) port to monitor the temperature inside the vessel. Two pressure sensors 16 (Heise Model DXD series, Ashcroft Inc., Stratford, Conn., USA) are installed to the fluid injection port 11 and the fluid discharge port 13 to monitor the inlet and outlet pressures during the course of the experiment. The fluid discharge port 13 is connected to a rear pressure gauge 63 (BPR, Tescom 26-1700 series, Emerson Electric Co., St. Louis, Mo., USA) which controls the outlet pressure during the depressurization process. The fluid generated from the hydrate sample flows to the separator 67, mass of water is measured in a scale 65 and the separated methane gas is collected into a gas collector 70.

In one embodiment of the disclosure, an X-ray CT scanner (Optima CT660, GE Health, Little Chalfont, U.K.) is used to image the internal changes in sediment during the experiment. An X-ray CT provides spatially analyzed quantitative information on X-ray attenuation characteristics of the scanned area, which can be related to density through calibration. The data is typically displayed as a 2-D or 3-D image. The scanning length is about 250 mm, so that the scan covers the entire length of the sediment and some GB layers. The time required for each scan is about 90 seconds, which justifies the assumption that there was no or minimal internal change during each scan and that the depressurization process could be properly captured. The maximum resolution of the X-ray CT scanner is about 100 μm and the slice spacing (or slice thickness) is 625 μm. All slice images obtained in the present disclosure are composed of 512×512 pixels with a pixel size of 107 μm and a slice thickness of 625 μm. The total number of slices obtained covers 380-400 sediments completely. Scanning is performed with controlled current and voltage values of the X-ray source, 120 kV-210 mA and 120 kV-250 mA.

Pre-calibration tests are performed with a material having a known density placed inside the high-pressure vessel to correlate X-ray CT values with density values. Air, water, quartz, aluminum alloy (AL6061), Ultra High Molecular Weight Polyethylene (UHMW-PE), High Density Polyethylene (HDPE), Polycarbonate (PC), Monocast Nylon (MC), Polyethylene Terephthalate (PET), Nailcast Poly Acetal (POM-C) and polyvinylidene fluoride (PVDF) are used as materials of known density.

Referring to FIG. 4, a sample molded initially having a water content of 5% is put into a high pressure cell 10, and glass beads 3 are stacked on both ends thereof so as to prevent the sample from moving. The high pressure cell 10 is then placed in a constant temperature and humidity chamber and saturated with methane gas at 12° C., just before the gas hydrate is produced. After the saturation process is completed, the high pressure cell 10 is entirely cooled to form a gas hydrate in the sample 1. Then, water is injected and made into a saturated state in order to simulate a gas hydrate layer. Then, the depressurization method is applied and the gas hydrate is dissociated and the entire process is photographed by an X-ray CT. The temperature and pressure conditions in the overall experiment are briefly shown in FIG. 4. In addition, an X-ray CT image of sample 2 is shown in FIG. 5 as a representative example in order to show an image observed through X-ray CT in each process.

The newly designed method in one embodiment of the present disclosure quantitatively analyzes the fines migration in a multiphase flow such as the gas hydrate production process by analyzing on a voxel-scale based on the different density of water and gas.

i) Obtaining an X-Ray CT Image

Referring to FIG. 4 and FIG. 5, X-ray CT images were obtained sequentially during the preparation of the experiment, gas injection in step 1, gas hydrate formation in step 2, water injection in step 3, and sequential depressurization production in step 4.

Periodic X-ray CT imaging at the stepwise depressurization step can be used to track temporal changes in fines content according to the sample, and post-dissociation sampling provides only endpoint information. Hydrates may be formed through depressurization during a preparation process of a precipitate, and thereby five components including sand, fine particles, water, methane hydrate and free methane gas may be included in one voxel. Therefore, in addition to the X-ray CT images obtained in the sample preparation step and the depressurization step, the calculation of mass of fine particles in each voxel requires preliminary information and additional information including the amount of generated water and the position of the gas bubbles (or gas voxels). The post-experiment sampling results were used to calculate a calibration coefficient. Here, for simplifying purposes, a density difference between hydrate and water was not assumed, and the total volume occupied by residual gas bubbles was equal to the volume of water generated in the time step, and these residual bubbles were uniformly distributed in gas voxels. When reviewing the image set obtained in the post-depressurization step (Step J) of Sample 1, the voxel scale analysis procedure is as follows.

ii-1) X-Ray CT Image Analysis Step (Sample Preparation Process)

Referring to FIG. 6, an X-ray CT image of a step previous to gas hydrate formation (after gas injection) is obtained and an analysis based on a voxel scale is performed. In this process, several assumptions are required and the mass, water content, and fines content of each component can be obtained. Assumptions are required in this process, wherein the first assumption is that water and fine particles are homogeneously distributed throughout the sample, and the second assumption is that since the sand particles don't move due to the very slow rate of depressurization, there is no change to the mass of sand per voxel ($M_{sand}$).

Assuming that the initial mixing ratio (water content w and fines content $FC_{ini}$) and water and fine particles are homogeneously dispersed, using the slice images obtained after gas injection (before the formation of gas hydrate, i.e. after step 1 of FIG. 4), the mass of sand per voxel ($M_{sand}$) can be obtained. The mass of sand per voxel is assumed to be constant in the depressurization process because the flow rate of the fluid due to depressurization is sufficiently low at a maximum of 3.2 mL/min.

ii-2) X-Ray CT Image Analysis Step (Depressurization Process)

Referring to FIGS. 7 and 8, when the depressurization process for producing gas hydrate is performed on a sample, the density of the sample is decreased and a change of an X-ray CT image showing the degree of attenuation due to the density is caused. Such a change is largely due to the dissociation of gas hydrate, the migration of sand particles, the formation of gas bubbles, and fines migration. The migration of the sand is negligible because the depressurization rate is very small at ~3 ml/min. The gas hydrate is relatively small in quantity and has a density of ~0.9 g/cm$^3$, which is not much different from water (1.0 g/cm$^3$). Therefore, among the four causes of density change, that is, changes in X-ray CT images, gas bubble generation and fine particle movement due to gas hydrate dissociation may be seen as the main causes of X-ray CT image changes. Since the position of the gas bubbles can be known by classifying it based on the threshold value obtained by histogram analysis, it is only necessary to finally calculate the volume of the gas bubble.

Since the total volume of gas bubbles is the same as the volume of water produced at that time, the volume of each gas voxel can be regarded as the volume of water divided by the number of voxels containing gas in the whole sample. With this method, once the gas volume has been stored in the voids, the voids become filled with fine particles and water only. Since the volume of the pores can be obtained by using the weight of the sand particles, the amount of fine particles in a certain volume can be calculated to determine the mass of the fine particles in each voxel.

From a slice image obtained in the post-depressurization step (step J), the bulk density of each voxel can be calculated from the CT value. Therefore, the total mass per voxel in the post-depressurization step, $M_{total\_J}$, can be obtained. Whether the voxel has free gas is already known through a threshold-based analysis (see FIG. 7). If the voxel contains gas, the gas volume per voxel ($V_{gas}$) is assumed to be equal to the total volume of water produced divided by the number of gas voxels. Then, since the gas volume is replaced by water, the total mass in the post-depressurization step becomes $M'_{total\_J} = M_{total\_J} + \rho_w V_{gas}$. If there is no gas, $M'_{total\_J} = M_{total\_J}$ can be calculated.

Since the void mass in the post-depressurization step is defined as the sum of the mass of the fine particles and the mass of water, the void mass can be expressed as $M_{void\_J} = M_{fine\_J} + M_{water\_J}$, which can be calculated as $M'_{total\_J} - M_{sand}$. The volume of the void can be calculated as $V_{void} = V_{total} - V_{sand} = V_{total} - M_{sand}/(G_s \cdot \rho_w)$ and $G_s$ is the specific density of the sediment particles.

iii) Calculation and Calculation of Fines Content

Referring to FIG. 9 and FIG. 10, the mass of the void, when saturated with water only, can be used to calculate the fines content compared to the final step of depressurization. The calculated fines content is calculated by comparing with the result of sampling after the experiment, and the calculated calibration coefficient is applied to finally calculate the fines content.

The void mass ($M_{void} = V_{void} \rho_w$), filled with water only, can be calculated as $\Delta M = M_{void\_J} - M_{void} = M_{fines\_J}(1 - 1/G_s)$ since it can be compared with the void mass $M_{void\_J}$ at the post-depressurization step. Therefore, the fines content (FC) in the post-depressurization step (Step J) is calculated as $FC_J = M_{fines\_J}/(M_{fines\_J} + M_{sand})$.

In the post-depressurization step, the fines content ($FC_J$) is calibrated as $FC_{J\_calibrated} = \alpha \cdot FC_J + \beta$ using a size calibration parameter α and an offset parameter β. The calibration factors α and β are determined by comparing a fines content, obtained from the post-experiment sampling, with an average fine particle content of the section through a least-square fitting method. The voxel-based analysis using X-ray CT images is limited to the area where the sediment samples are located, except for the glass bead layers on both sides of the high-pressure cell. The results of the analysis of the corrected fines content are shown in FIG. 9.

iv) Estimating the Results of the Analysis of Fines Migration

Referring to FIG. 11, it is possible to estimate the change of the fines content at each position of the sample in each depressurization step using the calculated fines content calculation results.

FIGS. 6, 8 and 10 summarize the voxel-based analysis method used to estimate the fines content. When the size calibration parameter α was 0.35, and the offset parameter β was 5.4, it was shown to be the best fit for the sample used in the analysis. One of the main results of the analysis is that the glass bead area has higher gas saturation due to the relatively large void size compared to the sediment layer. As a result, the gas voxel in the glass bead area has a larger amount of gas than the gas voxel in the region where the sediment layer exists, and the size calibration parameter α has a value ranging from 0.3 to 0.4.

Even after calibrating the fines content by using the calibration coefficients α and β, there was a large difference from the sampling results at some positions. This overestimation of the fine particle content is mainly due to overestimation of the gas amount. As the volume of gas is overestimated, the total volume increases and the fines content also increases. Due to the change in the sand sample structure that is not compact, the sediment may increase in porosity or the dry density may decrease and the fines content may increase. On the other hand, an underestimation of the gas volume can lessen the fine particle content in practice. For example, in the 33 to 55 mm section of FIG. 9 (Sample 1), the calculated fines content was higher than the sampling result. It is presumed that the effect of depressurization on the structural change of the sand sample around the glass bead area of the injection site and the effect of overestimation of the gas voxel are considered to be influential. Since the difference between the results of the analysis of fines content and the result of sampling analysis appears partly around the glass bead area, the analysis area is limited to the area where the sediment is located. Since there is a partially mixed region always having a constant thickness at a boundary surface between the glass bead area and the sediment sample, the voxel-based analysis method must be applied cautiously in regards to the edges and boundaries of the sediment.

A system 100 for carrying out a method of analyzing fines migration in a multiphase flow in a sediment layer using an X-ray CT image according to an embodiment of the present disclosure includes, an X-ray CT imaging part 110 for taking a fines migration image in a sediment layer; and a server 120 for executing a fines migration analysis method using a photographed image of the X-ray CT imaging part, wherein the server 120 includes, an input part 122 for applying a photographed image taken by the X-ray CT imaging part 110; an editing part 123 for removing noise of the photographed image in the input part 122, according to an algorithm of at least one preset gas hydrate formation amount predicting method program; an analyzer 124 for analyzing the fines migration in the photographed image from which the noise is removed; a calculating part 125 for calculating the fines migration from analysis data of the analyzer 124; a calibrating part 126 for calibrating the fines migration from calculation data of the calculating part 125; a result part 127 for calculating a fines migration result from calibration data of the calibrating part 126; a determination part 130 for determining a fines migration analysis result based on the results from the result part 127 and for saving the photographed image in a storage area which is classified according to state depending on the determined result; and a communication part 140 for transmitting a message informing the determined result to a pre-registered terminal.

The operation of a system 100 for implementing a method of analyzing fines migration in a multiphase flow in a sediment layer using an X-ray CT image according to an embodiment of the present invention will be described.

Referring to FIG. 12, a system 100 for analyzing fines migration in a multiphase flow in a sediment layer using an X-ray CT image includes an X-ray CT imaging part 110 and a server 120.

The X-ray CT imaging part 110 takes an image of fines migration in a sediment layer.

The server 120 includes an input part 122, an editing part 123, an analyzer 124, a calculating part 125, a calibrating part 126, and a result part 127. The method of analyzing fines migration is executed using the images taken by the X-ray CT imaging part 110.

The input part 122 allows the photographed image taken by the X-ray CT imaging part 110 to be applied.

The editing part 123 removes the noise of the photographed image according to an algorithm of at least one preset fines migration analysis method program input in the input unit 122.

The analyzer 124 analyzes the fines migration in the photographed image from which the noise is removed.

The calculating unit 125 calculates the fines migration in an analysis data of the analysis unit 124.

The calibrating unit 126 calibrates the fines migration in the calculation data of the calculating part 125.

The result part 127 calculates a fines migration result from the calibration data of the calibrating part 126.

The system 100 of analyzing fines migration in a multiphase flow in a sediment layer using an X-ray CT image includes a determination part 130 and a communication part 140. The determination part 130 and the communication part 140 may be configured independently of the server 120 or may be included in the server 120.

The determination part 130 determines the result of the fines migration analysis based on the result of the result part 127 and saves the photographed image in a storage area classified according to state depending on the determination result.

The communication part 140 transmits a message informing the determined result to a pre-registered terminal.

Referring to FIG. 13, a program algorithm of a method of analyzing fines migration in a multiphase flow in a sediment layer using an X-ray CT image is shown.

An X-ray CT image shows that the density of each part increases through the analysis of gas hydrate formation. Using this, a program algorithm of a method of analyzing the amount of gas hydrate generated, for each slice, is shown in FIG. 13. First, an X-ray CT image taken during a gas hydrate formation process is converted into a text image for each slice. In the converted slices, the X-ray CT values of pixel positions can be seen. These X-ray CT values can be converted to density using a density calibration equation. When the average density is calculated and is set as a representative density of each slice, the density increase can be calculated for each slice. By multiplying the thickness and size of the slices having such density, the increase in weight for each slice can be calculated. The increase in weight can be considered to be caused from the formation of gas hydrate since other than methane gas, a closed state was maintained.

A method of analyzing fines migration in a multiphase flow in a sediment layer using an X-ray CT image according to an embodiment of the present disclosure, can be implemented as a program for analyzing fines migration in a multiphase flow in a sediment layer using an X-ray CT image.

According to the present disclosure, it is possible to increase the applicability of a visualization technique by diversifying the particle size of sand sediment layers and fine sediments that are flown in, to improve the technique for analyzing sediment particle migration in a multiphase flow, which improves the accuracy a monitoring technique.

While the present invention has been particularly shown and described with reference to exemplary embodiments thereof, it is evident that many alternatives, modifications and variations will be apparent to those skilled in the art. It will be understood by those skilled in the art that various changes in form and details may be made therein without departing from the spirit and scope of the invention as defined by the appended claims.

In addition, since the present invention can be embodied in various forms, and should not be construed as being limited to the embodiments set forth herein. Rather, these embodiments are provided so that this disclosure will be thorough and complete and will fully convey the concept of the invention to those skilled in the art, and the present disclosure will only be defined by the appended claims.

DESCRIPTION OF SYMBOLS

1: sample
3: glass bead
4: body part
10: high pressure cell
11: fluid injection port
13: fluid discharge port
15: temperature sensor
16: pressure sensor
18: screen
19: transparent screen
20: accumulator
30: methane cylinder
40, 50: syringe pump
63: rear pressure gauge
65: scale
67: separator
70: gas collector
100: fines migration analysis X-ray CT system
110: X-ray CT imaging part
120: server
122: input part
123: editing part
124: analyzer
125: calculating part
126: calibrating part
127: result part
130: determination part
140: communication part

What is claimed is:

1. A method of analyzing fines migration in a multiphase flow in a sediment layer using X-ray computed tomography (CT) image, comprising, preparing an X-ray CT image analysis sample;

analyzing an X-ray CT image during a depressurization process;

calibrating and calculating fines content; and estimating a fines migration analysis result.

2. The method of claim 1, wherein the preparing the X-ray CT image analysis sample comprises, obtaining an X-ray CT image after gas injection prior to gas hydrate production and performing a voxel-scale based analysis.

3. A non-transitory storage medium storing a computer program for implementing a method disclosed in claim 2.

4. The method of claim 1, wherein the preparing the X-ray CT image analysis sample is premised on, a first assumption that water and the fine particles are homogeneously distributed throughout the sample, and a second assumption that mass of sand per voxel ($M_{sand}$) is constant during the depressurization process.

5. A non-transitory storage medium storing a computer program for implementing a method disclosed in claim 4.

6. The method of claim 1, wherein the analyzing the X-ray CT image during the depressurization process comprises, classifying positions of gas bubbles based on threshold values obtained through a histogram analysis to calculate only the volume of the gas bubbles, and calculating the volume of fine particles that take up space within a constant volume as a volume of water divided by a number of voxels having gas therein of the entire sample, which is considered as a volume of each voxel, to calculate mass of the fine particles in each of the gas voxels.

7. A non-transitory storage medium storing a computer program for implementing a method disclosed in claim 6.

8. The method of claim 1, wherein the calibrating and calculating the fines content comprises, comparing the calculated fines content with a result of sampling after an experiment, to calculate a calibration coefficient, and finally calculating the fines content by applying the calibration coefficient.

9. A non-transitory storage medium storing a computer program for implementing a method disclosed in claim 8.

10. The method of claim 1, wherein the estimating the fines migration analysis result comprises, estimating a change in the fines content at each position of the sample in each step of the depressurization process by using calculation results of the calculated fines content.

11. A non-transitory storage medium storing a computer program for implementing a method disclosed in claim 9.

12. The method of claim 1, wherein the preparing the X-ray CT image analysis sample further comprises, calculating Equation b-11 to Equation b-14, and $$M_{total0}=M_{sand}+M_{fines0}+M_{water} \quad \text{[Equation b-11]}$$

wherein, $M_{total0}$: total mass per voxel, $M_{sand}$: mass of sand per voxel, $M_{fines0}$: mass of fine particles per voxel, $M_{water}$: mass of water per voxel, $$w=M_{water}/(M_{sand}+M_{fines0}) \quad \text{[Equation b-12]}$$

wherein, w: water content, $M_{water}$: mass of water per voxel, $M_{sand}$: mass of sand per voxel, $M_{fines0}$: mass of fine particles per voxel, $$FC_{ini}=M_{fines0}/(M_{sand}+M_{fines0}) \quad \text{[Equation b-13]}$$

wherein $FC_{ini}$: initial fines content, $M_{fines0}$: mass of fine particles per voxel, $M_{sand}$: mass of sand per voxel, $$M_{sand}=(1-FC_{ini}) \cdot M_{total0}/(1+w) \quad \text{[Equation b-14]}$$

wherein, $M_{sand}$: mass of sand per voxel, $FC_{ini}$: initial fines content, $M_{total0}$: total mass per voxel, w: water content.

13. A non-transitory storage medium storing a computer program for implementing a method disclosed in claim 12.

14. The method of claim 1, wherein the analyzing the X-ray CT image during the depressurization process comprises, calculating Equation b-21 to Equation b-26, and $$M_{total\_J}=M_{sand}+M_{fines\_J}+M_{water\_J} \quad \text{[Equation b-21]}$$

wherein, $M_{total\_J}$: total mass per voxel after depressurization, $M_{sand}$: mass of sand per voxel, $M_{fines\_J}$: mass of fine particles per voxel after depressurization, $M_{water\_J}$: mass of water per voxel after depressurization, $$M'_{total\_J}=M_{total\_J}+\rho_w \cdot V_{gas} \quad \text{[Equation b-22]}$$

wherein, $M_{total\_J}$: total mass per voxel after depressurization, $M'_{total\_J}$: total mass per voxel after water replaces gas by volume after depressurization, $\rho_w$: bulk density of voxel, $V_{gas}$: volume of gas per voxel, $$M'_{total\_J}-M_{sand}=M_{void\_J} \quad \text{[Equation b-23]}$$

wherein, $M'_{total\_J}$: total mass per voxel after water replaces gas by volume after depressurization, $M_{sand}$: mass of sand per voxel, $M_{void\_J}$: void mass per voxel after depressurization, $$M_{void\_J}=M_{fines\_J}+M_{water\_J} \quad \text{[Equation b-24]}$$

wherein, $M_{void\_J}$: void mass per voxel after depressurization, $M_{fines\_J}$: mass of fine particles per voxel after depressurization, $$V_{sand}=M_{sand}/G_s \cdot \rho_w \quad \text{[Equation b-25]}$$

wherein, $V_{sand}$: volume of sand per voxel, $M_{sand}$: mass of sand per voxel, $G_s$: specific density of sediment particle, $\rho_w$: bulk density of voxel, $$V_{void}=V_{total}-V_{sand} \quad \text{[Equation b-26]}$$

wherein, $V_{void}$: void volume per voxel, $V_{total}$: total volume per voxel, $V_{sand}$: volume of sand per voxel.

15. A non-transitory storage medium storing a computer program for implementing a method disclosed in claim 14.

16. The method of claim 1 wherein the calibrating and the calculating the fines content comprises, calculating Equation c-1 to Equation c-5, and $$\Delta M=M_{void\_J}-M_{void} \quad \text{[Equation c-1]}$$

wherein, $M_{void}$: void mass per voxel, $M_{void\_J}$: void mass per voxel after depressurization, $\Delta M$: difference of void mass per voxel before and after depressurization, $$M_{fines\_J}=\Delta M \cdot G_s/(G_s-1) \quad \text{[Equation c-2]}$$

wherein, $M_{fines\_J}$: mass of fine particles per voxel after depressurization, $\Delta M$: difference of void mass per voxel before and after depressurization, $G_s$: specific density of sediment particle, $$FC_J=M_{fines\_J}/(M_{fines\_J}+M_{sand}) \quad \text{[Equation c-3]}$$

wherein, $FC_J$: fines content after depressurization, $M_{fines\_J}$: mass of fine particles per voxel after depressurization, $M_{sand}$:
mass of sand per voxel, $$FC_J=(M'_{total\_J}-V_{total} \cdot \rho_w) \cdot G_s/(G_s-1)-M_{sand} \quad \text{[Equation c-4]}$$

wherein, $FC_J$: fines content after depressurization, $M'_{total\_J}$: mass per voxel after depressurization, $V_{total}$: total volume per voxel, $\rho_w$: density of water, $G_s$: specific density of sediment particle, $M_{sand}$: mass of sand per voxel, $$FC_{J\_calibrated}=\alpha \cdot FC_J+\beta \quad \text{[Equation c-5]}$$

wherein, $FC_{J\_calibrated}$: calibrated fines content, $\alpha$: calibration parameter, $FC_J$: fines content after depressurization, $\beta$: offset parameter.

17. A non-transitory storage medium storing a computer program for implementing a method disclosed in claim 16.

18. A non-transitory storage medium storing a computer program for implementing a method disclosed in claim 1.

19. An apparatus for analyzing fines migration in a multiphase flow in a sediment layer using X-ray computed tomography (CT), comprising, a high pressure cell provided with, a body part in which a center sample is located, a fluid injection port on one side of the body part, and a fluid discharge port on an opposite side of the body part;
a temperature sensor and a pressure sensor provided in the fluid injection port and the fluid discharge port; and
a server configured to:
prepare an X-ray CT image analysis sample;
analyze an X-ray CT image during a depressurization process;
calibrate and calculate fines content; and
estimate a fines migration analysis result.

20. The apparatus of claim 19 further comprising,
a methane cylinder for supplying methane, connected to the fluid injection port;
a syringe pump connected to the methane cylinder;
a rear pressure gauge connected to the fluid discharge port;
a scale for measuring only mass of water from gas and water discharged through an outlet of the rear pressure gauge; and
a gas collector for collecting dry gas discharged through the outlet of the rear pressure gauge.

21. The apparatus of claim 19 wherein the high pressure cell further comprises,
a screen disposed between the outlet of the fluid discharge port and the center sample; and
a transparent window through which an inner part of the outlet of the fluid discharge port is reflected.

22. The apparatus of claim 21 further comprising,
a glass bead drawn into the body part.

23. A system for carrying out a method of analyzing fines migration in a multiphase flow in a sediment layer using an X-ray CT image, comprising,
an X-ray CT imaging part for taking a fines migration image in a sediment layer; and
a server for executing a fines migration analysis method using a photographed image of the X-ray CT imaging part, wherein
the server comprises,
an input part for applying a photographed image taken by the X-ray CT imaging part;
an editing part for removing noise of the photographed image in the input part, according to an algorithm of at least one preset gas hydrate (GH) formation amount predicting method program;
an analyzer for analyzing the fines migration in the photographed image from which the noise is removed;
a calculating part for calculating the fines migration from analysis data of the analyzer;
a calibrating part for calibrating the fines migration from calculation data of the calculating part;
a result part for calculating a fines migration result from calibration data of the calibrating part;
a determination part for determining a fines migration analysis result based on the results from the result part and for saving the photographed image in a storage area which is classified according to state depending on the determined result; and
a communication part for transmitting a message informing the determined result to a pre-registered terminal.

* * * * *